United States Patent
Graves et al.

(10) Patent No.: US 10,144,537 B2
(45) Date of Patent: Dec. 4, 2018

(54) SYSTEMS AND METHODS FOR DISPENSING RADIOACTIVE LIQUIDS

(71) Applicant: Mallinckrodt Nuclear Medicine LLC, Hazelwood, MO (US)

(72) Inventors: Kevin B. Graves, Catawissa, MO (US); Bryan S. Petrofsky, St. Louis, MO (US); Brian J. Morton, St. Louis, MO (US); Matthew S. Muraczewski, Dardenne Prairie, MO (US); Lars Lindskog, Ballwin, MO (US); Stephen C. Iverson, St. Charles, MO (US); Rafael A. Martinez, St. Peters, MO (US)

(73) Assignee: Mallinckrodt Nuclear Medicine LLC, Maryland Heights, MO (US)

( * ) Notice: Subject to any disclaimer, the term of this patent is extended or adjusted under 35 U.S.C. 154(b) by 0 days.

(21) Appl. No.: 15/365,279

(22) Filed: Nov. 30, 2016

(65) Prior Publication Data

US 2018/0148200 A1    May 31, 2018

(51) Int. Cl.
*B01J 19/08* (2006.01)
*B65B 3/00* (2006.01)
(Continued)

(52) U.S. Cl.
CPC ............ *B65B 3/003* (2013.01); *A61M 5/178* (2013.01); *B65B 3/12* (2013.01); *B67D 7/02* (2013.01);
(Continued)

(58) Field of Classification Search
CPC ......... B01J 19/08; B01J 19/081; B65B 3/003; G21F 7/00; G21F 7/04; G21F 7/06; G21F 7/068
See application file for complete search history.

(56) References Cited

U.S. PATENT DOCUMENTS

| | | |
|---|---|---|
| 3,915,651 A | 10/1975 | Nishi |
| 4,101,283 A | 7/1978 | Sundstrom |

(Continued)

FOREIGN PATENT DOCUMENTS

| | | |
|---|---|---|
| JP | 2006325826 A | 12/2006 |
| WO | 9404415 A1 | 3/1994 |

(Continued)

OTHER PUBLICATIONS

International Search Report and Written Opinion of the International Searching Authority regarding PCT/US2016/069203 dated Aug. 23, 2017; pp. 1-12.

*Primary Examiner* — Jill A Warden
*Assistant Examiner* — Dwayne K Handy
(74) *Attorney, Agent, or Firm* — Armstrong Teasdale LLP

(57) ABSTRACT

Systems and methods for dispensing radioactive liquids using a liquid dispensing apparatus are described. The apparatus includes a support arm rotatable about a rotation axis, an actuator operatively connected to the support arm and configured to at least one of rotate the support arm about the rotation axis and displace the support arm in a direction parallel to the rotation axis, and a pipette assembly mounted to the support arm. The pipette assembly includes a pipette tip defining an opening through which liquids are aspirated and dispensed, a piston, and a stepper motor operatively connected to the piston to control linear displacement of the piston.

20 Claims, 10 Drawing Sheets

(51) Int. Cl.
  *A61M 5/178*   (2006.01)
  *B65B 3/12*    (2006.01)
  *B67D 7/02*    (2010.01)
  *G21F 5/14*    (2006.01)
  *G21F 7/06*    (2006.01)
  *G21F 5/015*   (2006.01)
  *G21G 1/00*    (2006.01)

(52) U.S. Cl.
  CPC ................ *G21F 5/015* (2013.01); *G21F 5/14* (2013.01); *G21F 7/068* (2013.01); *G21G 1/0005* (2013.01)

(56) References Cited

U.S. PATENT DOCUMENTS

| | | |
|---|---|---|
| 4,459,267 A | 7/1984 | Bunce et al. |
| 4,555,957 A | 12/1985 | Frankel et al. |
| 4,586,546 A | 5/1986 | Mezei et al. |
| 5,046,539 A | 9/1991 | MacLeish et al. |
| 5,369,566 A | 11/1994 | Pfost et al. |
| 6,143,252 A | 11/2000 | Haxo, Jr. et al. |
| 7,284,454 B2 | 10/2007 | Cote |
| 7,421,913 B2 | 9/2008 | Belgardt et al. |
| 7,429,360 B2 | 9/2008 | Kureshy et al. |
| 7,867,752 B1 | 1/2011 | Greenberger et al. |
| 8,114,361 B2 | 2/2012 | Reichmuth |
| 8,435,738 B2 | 5/2013 | Holmes |
| 8,580,210 B2 | 11/2013 | Katsumi et al. |
| 9,347,586 B2 | 5/2016 | Williams et al. |
| 9,404,876 B2 | 8/2016 | Broga et al. |
| 2004/0047765 A1 | 3/2004 | Gordon et al. |
| 2005/0056713 A1* | 3/2005 | Tisone ............... B01D 19/0047 239/690 |
| 2005/0214172 A1 | 9/2005 | Burgisser |
| 2006/0249542 A1 | 11/2006 | Allen |
| 2009/0016931 A1 | 1/2009 | Seino et al. |
| 2009/0181463 A1 | 7/2009 | Chen |
| 2012/0096929 A1 | 4/2012 | Baek |
| 2013/0144051 A1* | 6/2013 | Mueller ............... B01J 19/004 536/122 |
| 2013/0266952 A1 | 10/2013 | Goemann-Thos et al. |
| 2014/0030167 A1 | 1/2014 | Yamashita et al. |
| 2016/0216286 A1 | 7/2016 | Holmes et al. |

FOREIGN PATENT DOCUMENTS

| | | |
|---|---|---|
| WO | 2005121780 A2 | 12/2005 |
| WO | 2013069309 A1 | 5/2013 |

* cited by examiner

SYSTEMS AND METHODS FOR DISPENSING RADIOACTIVE LIQUIDS

FIELD

The field of the disclosure relates generally to liquid handling systems and, more particularly, to systems and methods for dispensing discrete volumes of radioactive liquids.

BACKGROUND

Radioactive material is used in nuclear medicine for diagnostic and therapeutic purposes by injecting a patient with a small dose of the radioactive material, which concentrates in certain organs or regions of the patient. Radioactive materials typically used for nuclear medicine include Germanium-68 ("Ge-68"), Strontium-87m, Technetium-99m ("Tc-99m"), Indium-111m ("In-111"), Iodine-131 ("I-131") and Thallium-201.

In the U.S., production of radiopharmaceuticals is regulated by the Current Good Manufacturing Practice (cGMP) regulations for human pharmaceuticals. During cGMP pharmaceutical (and other) manufacturing, it is sometimes desirable to accurately dispense low quantity target volumes of hazardous substances, such as radioactive liquids, from a source container into a clean destination container. For example, in the production of radiopharmaceuticals used in diagnostic imaging, a relatively large quantity of the radiopharmaceutical may be prepared in a source vial. In some applications, it is desirable to transfer the radiopharmaceutical from the source vial into a relatively clean vial, for example, for shipment to an end user. At least some known methods of transferring radioactive liquid from a source vial to a destination vial provide less than optimal accuracy and consistency, and/or expose the operator to nuclear radiation.

Accordingly, a need exists for a radioactive material handling system that provides improved accuracy and precision in transferring radioactive liquids, and reduces operator exposure to radiation.

This Background section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

BRIEF SUMMARY

In one aspect, a system for dispensing radioactive liquids includes a radiation containment chamber including an enclosure constructed of a radiation shielding material, and a liquid dispensing apparatus at least partly disposed in an interior of the enclosure. The liquid dispensing apparatus includes a support arm rotatable about a rotation axis, an actuator operatively connected to the support arm and configured to at least one of rotate the support arm about the rotation axis and displace the support arm in a direction parallel to the rotation axis, and a pipette assembly mounted to the support arm. The pipette assembly includes a pipette tip defining an opening through which liquids are aspirated and dispensed, a piston, and a stepper motor operatively connected to the piston to control linear displacement of the piston.

In another aspect, an apparatus for dispensing radioactive liquids includes a support arm rotatable about a rotation axis, an actuator operatively connected to the support arm and configured to at least one of rotate the support arm about the rotation axis and displace the support arm in a direction parallel to the rotation axis, and a pipette assembly mounted to the support arm. The pipette assembly includes a pipette tip defining an opening through which liquids are aspirated and dispensed, a piston, and a stepper motor operatively connected to the piston to control linear displacement of the piston. The apparatus is free of radiation-sensitive electronics.

In yet another aspect, a method of dispensing radioactive liquid using a dispensing apparatus including a pipette assembly mounted on a rotatable support arm is provided. The pipette assembly includes a pipette tip, a piston, and a stepper motor operatively connected to the piston. The method includes positioning the pipette assembly above a first vial using the support arm, aspirating a volume of radioactive liquid from a first vial by displacing the piston in a first direction using the stepper motor, rotating the support arm to position the pipette assembly above a second vial, and dispensing at least a portion of the volume of radioactive liquid into the second vial by displacing the piston in a second direction opposite the first direction using the stepper motor.

Various refinements exist of the features noted in relation to the above-mentioned aspects. Further features may also be incorporated in the above-mentioned aspects as well. These refinements and additional features may exist individually or in any combination. For instance, various features discussed below in relation to any of the illustrated embodiments may be incorporated into any of the above-described aspects, alone or in any combination.

BRIEF DESCRIPTION OF THE DRAWINGS

Corresponding reference characters indicate corresponding parts throughout the several views of the drawings.

DETAILED DESCRIPTION

Example systems and methods of the present disclosure facilitate dispensing small volumes of liquids (e.g., from 0.1 microliters (µL) up to 10 milliliters (mL)), while eliminating human error typically associated with manual dispensing. Embodiments of this disclosure are particularly suitable for dispensing small volumes of radioactive liquids, and facilitate dispensing such liquids safely, cleanly, accurately, and precisely. In particular, embodiments of the present disclosure facilitate automating the transfer of radioactive liquids from a source vial to a destination vial while avoiding or minimizing operator whole-body and extremity radiation exposure.

Figure 1:
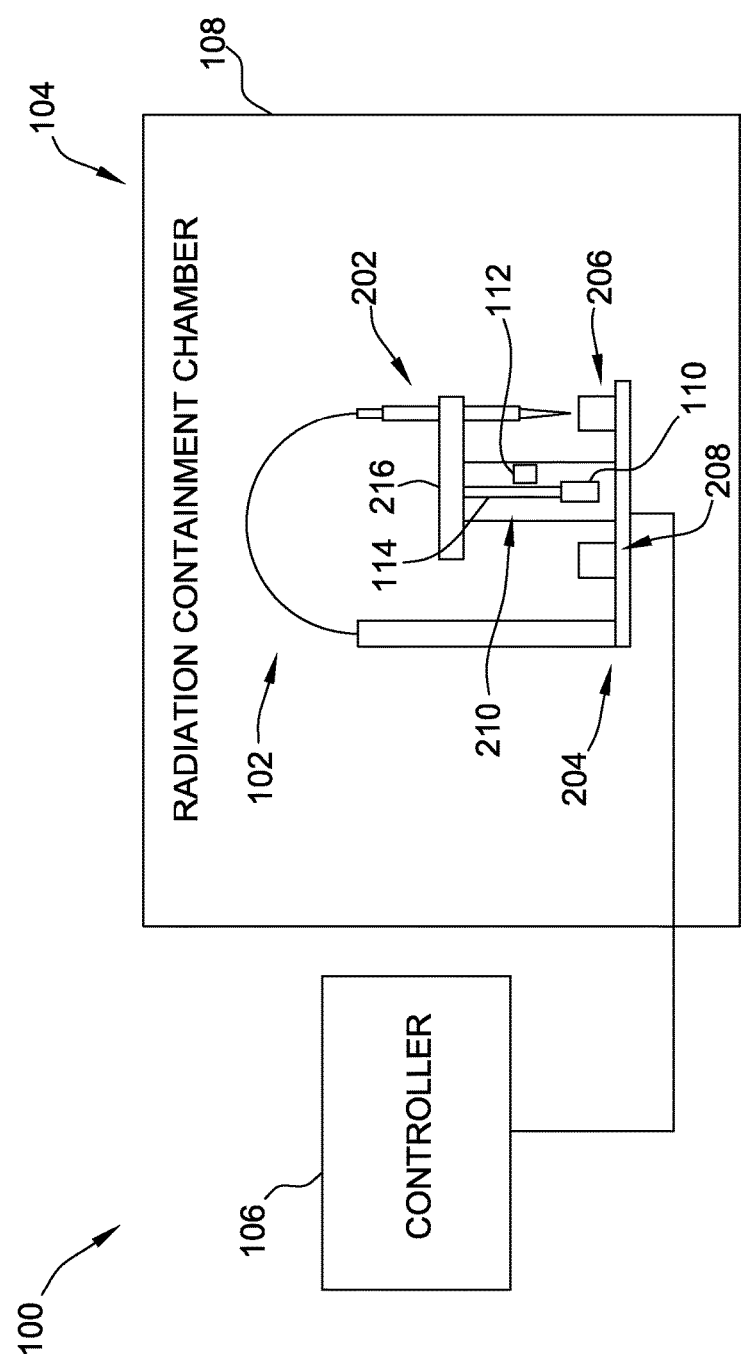
FIG. 1 is a schematic view of a system for dispensing liquids, such as radioactive liquids.

FIG. 1 is a schematic view of a system for dispensing liquids, indicated generally by reference numeral 100. Although the system 100 is described herein with reference to dispensing and transferring radioactive liquids, the system is not limited to dispensing radioactive liquids and may be used to dispense, transfer, or otherwise handle other liquids. The system 100 generally includes a liquid dispensing apparatus 102 enclosed within the interior of a shielded nuclear radiation containment chamber 104, also referred to herein as a "hot cell", and a computing device or controller 106 connected to the liquid dispensing apparatus 102 by a suitable communication link (e.g., a wired connection). The liquid dispensing apparatus 102 and the controller 106 are connected to a suitable power supply. Suitable power supplies include, for example and without limitation, a 120V AC power supply. As described further herein, the liquid dispensing apparatus 102 is configured to transfer precise amounts of radioactive liquids from one vial to another vial in response to control signals received from the controller 106.

The liquid dispensing apparatus 102 is enclosed within the containment chamber 104 to shield operators and radiation-sensitive electronics of the controller 106 from nuclear radiation emitted by radioactive materials within the containment chamber 104. The containment chamber 104 generally includes an enclosure 108 constructed of nuclear radiation shielding material designed to shield the surrounding environment from nuclear radiation. The enclosure defines an interior in which the liquid dispensing apparatus is positioned. Suitable shielding materials from which the containment chamber 104 may be constructed include, for example and without limitation, lead, depleted uranium, and tungsten. In some embodiments, the containment chamber 104 is constructed of steel-clad lead walls forming a cuboid or rectangular prism. Further, in some embodiments, the containment chamber 104 may include a viewing window constructed of a transparent shielding material. Suitable materials from which viewing windows may be constructed include, for example and without limitation, lead glass.

Figure 2:
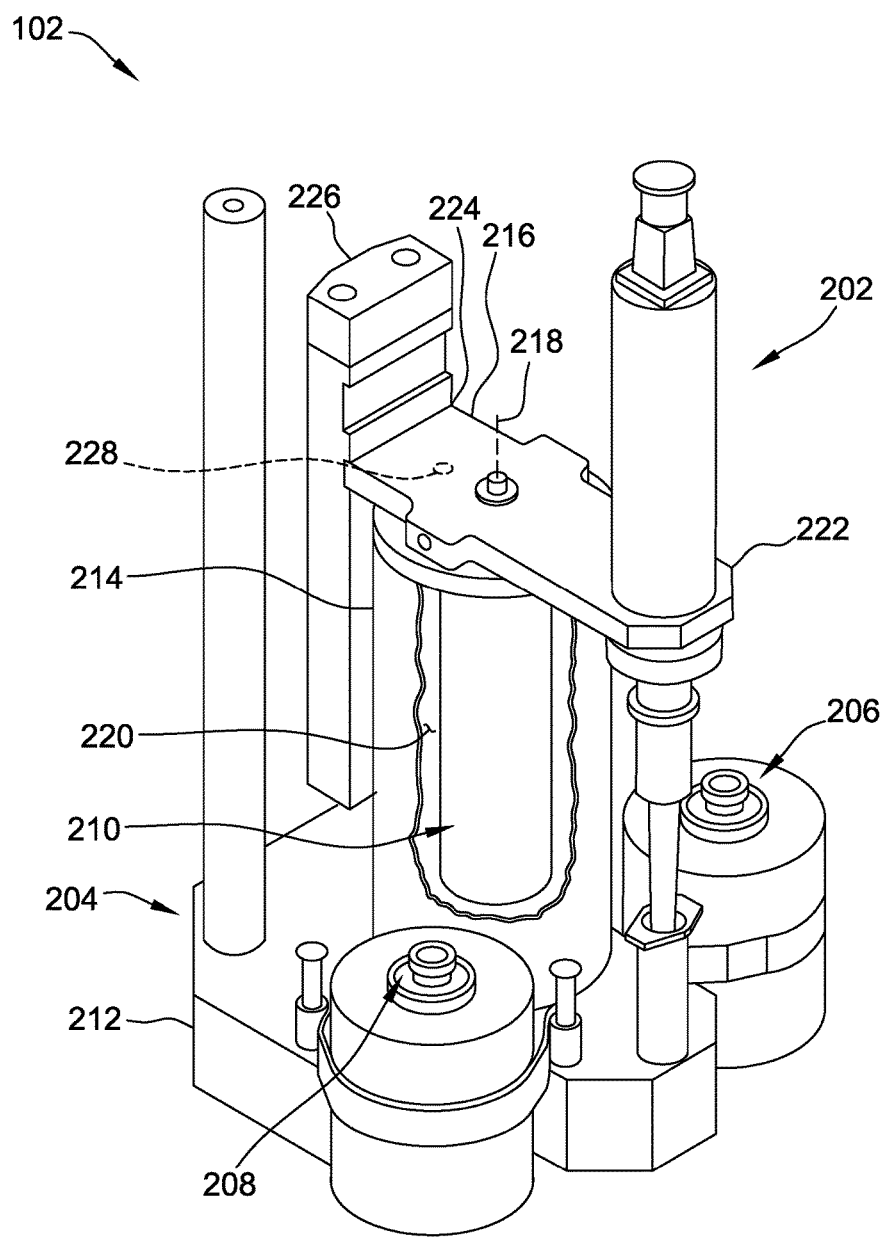
FIG. 2 is a perspective view of a liquid dispensing apparatus included in the system of FIG. 1.

With additional reference to FIG. 2, the liquid dispensing apparatus 102 generally includes a pipette assembly 202 mounted to a support frame 204, a source vial 206 (generally, a first vial), a destination vial 208 (generally, a second vial), and a dual-motion actuator 210 operatively connected to the pipette assembly 202 for positioning the pipette assembly 202 relative to the source vial 206 and the destination vial 208.

In the illustrated embodiment, the support frame 204 includes a base 212, a column 214 extending vertically upwards from the base 212, and a support arm 216 rotatably mounted at the top of the column 214 for rotation about a rotation axis 218.

The column 214 has a tubular construction defining an interior 220 of the support base 212. In the example embodiment, the dual-motion actuator 210 is positioned within the interior 220 of the column 214.

Figure 3:
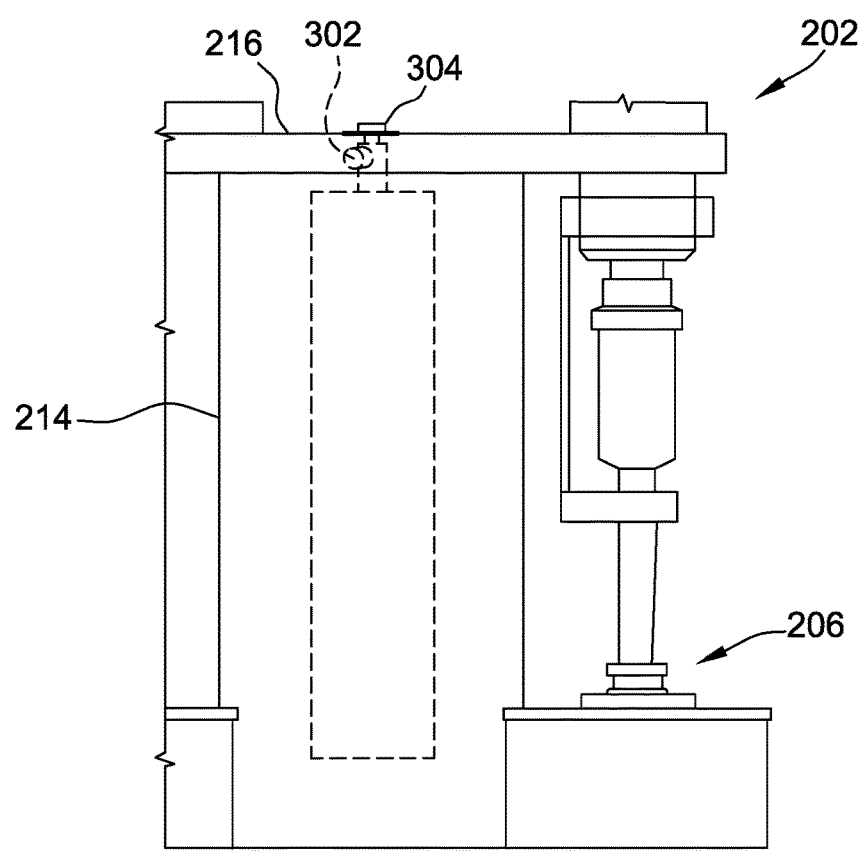
FIG. 3 is an enlarged view of a portion of the liquid dispensing apparatus shown in FIG. 2.

The support arm 216 is mounted at the top of the column 214, and is configured to rotate about the rotation axis 218 under the control of the dual-motion actuator 210. More specifically, as shown in FIG. 3, the support arm 216 is operatively connected to the dual-motion actuator 210 at the top of the column 214 by a compression fitting (e.g., a machined hole extending through the support arm 216), a set screw 302, and a locknut 304. In other embodiments, the support arm 216 may be operatively connected to the dual-motion actuator 210 by any other suitable connection means that enables the liquid dispensing apparatus 102 to function as described herein.

The support arm 216 extends radially outward from the top of the column 214 to opposing first and second ends 222, 224. The pipette assembly 202 is connected to the support arm 216 at the first end 222. In the example embodiment, the support arm 216 also includes a counterweight or counterbalance 226 connected at the second end 224 of the support arm 216 to maintain the support arm 216 in a horizontal orientation and facilitate smooth rotation about the rotation axis 218.

Components of the support frame 204, including, but not limited to, the base 212, the column 214, and the support arm 216, may be constructed from materials having a high tolerance to gamma and beta radiation. Suitable materials from which components of the support frame 204 may be constructed include, for example and without limitation, acrylic, polyvinylchloride (PVC), and polycarbonate. "High tolerance to gamma and beta radiation" means that the material can withstand a dose of at least 4 megarads (Mrads) of radiation without experiencing significant damage. Acrylic experiences significant damage at a radiation dose of about 5 Mrads, PVC experiences significant damage at a radiation dose of about 50 to 100 Mrads, and polycarbonate experiences significant damage at a radiation dose in excess of 100 Mrads.

The dual-motion actuator 210 is configured to control a vertical and rotational position of the support arm 216 and, consequently, a vertical and rotational position of the pipette assembly 202. More specifically, the dual-motion actuator 210 is configured to rotate the support arm 216 about the rotation axis 218, and to displace (e.g., raise and lower) the support arm 216 in a direction parallel to the rotation axis 218 (i.e., a vertical direction).

In the example embodiment, the dual-motion actuator 210 includes a first stepper motor 110 (shown in FIG. 1) that controls rotation of the support arm 216, and a second stepper motor 112 (shown in FIG. 1) that controls the vertical position of the support arm 216 and, consequently, the vertical position of the pipette assembly 202. In the example embodiment, the first stepper motor 110 is operatively connected to the support arm 216 via a rotatable shaft 114 that protrudes from a top of the column 214. The rotatable shaft 114 is received within the compression fitting and secured to the support arm 216 by the set screw 302 and the locknut 304. Operation of the first stepper motor 110 causes the shaft 114 to rotate, and thereby rotate the support arm 216 about the rotation axis 218. The second stepper motor 112 is operatively connected to the support arm 216 (e.g., via the rotatable shaft 114). Moreover, the second stepper motor 112 is connected to the support arm 216 through a linear actuator (not shown) such that operation of the second stepper motor 112 raises and lowers the support arm 216 (and, consequently, the pipette assembly 202). In some embodiments, the shaft 114 is connected to the first stepper motor 110 by a spline joint to enable the shaft 114 to maintain engagement with the first stepper motor 110 while being raised and lowered by the second stepper motor 112. The rotational direction and speed of the first and second stepper motors 110, 112 are controlled by the controller 106 such that the dual-motion actuator 210 selectively controls a rotational position and vertical height of the support arm 216 and the pipette assembly 202.

The first and second stepper motors 110, 112 may have any suitable stepper motor construction that enables the liquid dispensing apparatus 102 to function as described herein. Generally, each of the first and second stepper motors 110, 112 includes a plurality of motor windings or coils and a rotor that rotates in response to the motor windings being sequentially energized. Rotation of the rotor occurs in discrete, equal steps or angular distances, the number of steps generally corresponding to the number of times the motor windings are energized. In this way, the first and second stepper motors 110, 112 can be rotated and/or held at a desired position without the use of position feedback sensors. In the example embodiment, the first and second stepper motors 110, 112 do not include any electronics, such as position feedback sensors (e.g., resolvers, encoders, or optical sensors). One example of a suitable actuator suitable for use as the first and/or second stepper motors 110, 112 includes the Haydon™ dual motion linear actuator model LR43MH4R-2.33-940, available from Haydon Kerk Motion Solutions.

The pipette assembly 202 is disposed at the first end 222 of the support arm 216, which is operatively connected to the dual-motion actuator 210. The vertical height and rotational position of the support arm 216 and, consequently, the pipette assembly 202, are controlled by operation of the dual-motion actuator 210. In this way, the pipette assembly 202 can be rotated into different rotational positions relative to the rotation axis 218, for example, above the source vial 206, above the destination vial 208, or in a home position in between the source and destination vials 206, 208. Additionally, the pipette assembly 202 can be raised and lowered relative to the source vial 206 and the destination vial 208.

Figure 4:
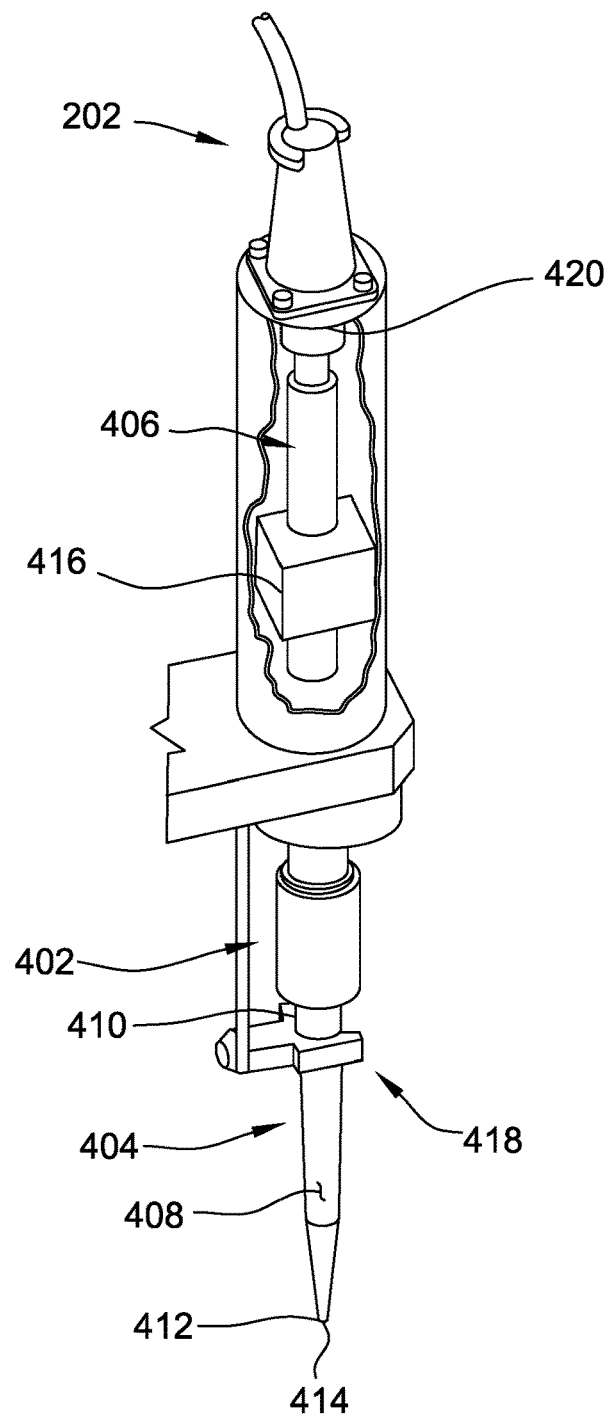
FIG. 4 is a perspective view of a pipette assembly included in the liquid dispensing apparatus shown in FIG. 2.

With additional reference to FIG. 4, the pipette assembly 202 is configured to aspirate and dispense discrete volumes of liquid to effect liquid transfer between the source vial 206 and the destination vial 208. The pipette assembly 202 includes a pipette body 402, a pipette tip 404 connected to the pipette body 402, and a linear actuator 406 operatively connected to the pipette body 402.

Figure 5:
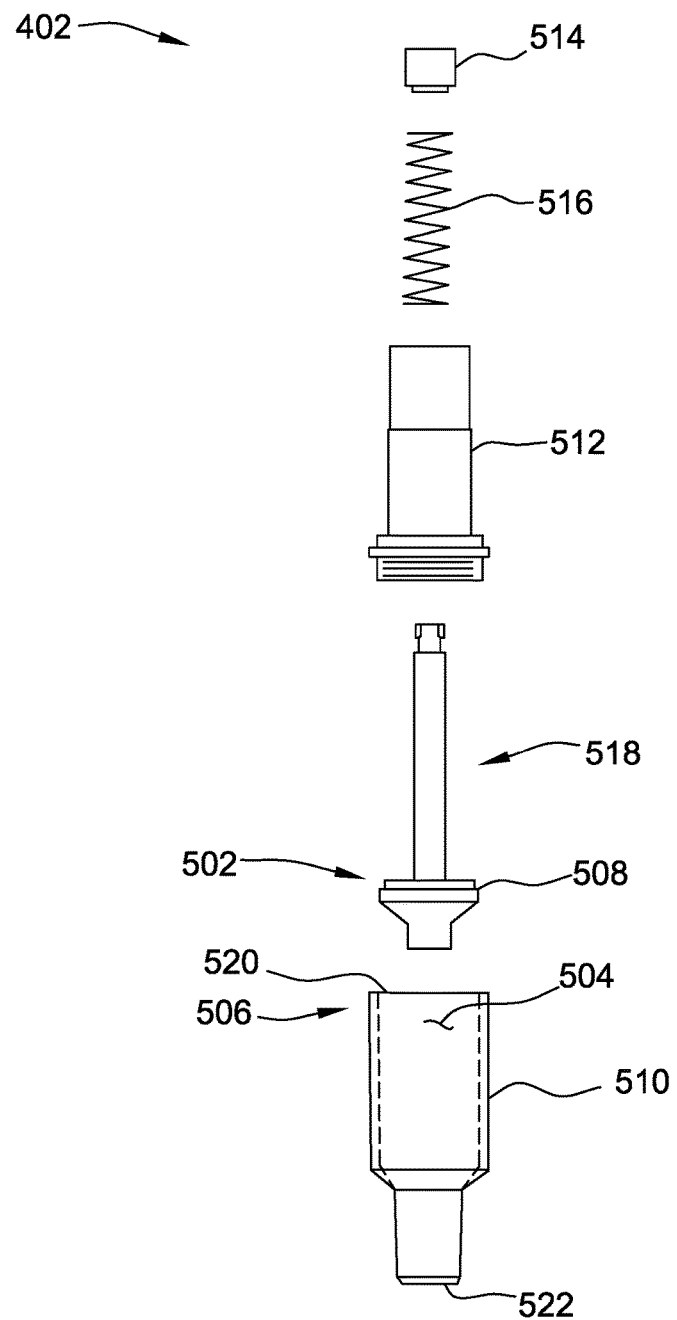
FIG. 5 is an exploded view of a pipette body included in the pipette assembly shown in FIG. 4.

FIG. 5 is an exploded view of the pipette body 402. As shown in FIG. 5, the pipette body 402 includes a plunger or piston 502 that reciprocates within a piston chamber 504 defined by a piston housing 506 of the pipette body 402. The piston 502 includes an annular seal 508 that seals against a cylindrical sidewall 510 of the piston housing 506 to prevent fluid flow past the piston 502. Linear movement of the piston 502 within the piston chamber 504 generates pressure differentials that allow liquids to be aspirated into and dispensed from the pipette tip 404.

In the example embodiment, the pipette body 402 also includes a piston guide 512, a piston mount 514, and a spring 516 connected between the piston guide 512 and the piston mount 514. The piston guide 512 engages a stem 518 of the piston 502 to maintain alignment of the piston 502 within the piston chamber 504. The piston guide 512 is connected to a first end 520 of the piston housing 506 by a suitable fastening mechanism, such as a threaded connection. The piston mount 514 is operatively connected to the piston 502 (e.g. via the piston stem 518), and is accessible from the exterior of the pipette body 402 to enable manipulation of the piston 502. The spring 516 is compressed between the piston mount 514 and the piston guide 512, and biases the piston mount 514 and the piston 502 towards a fully retracted position. Examples of commercially available pipette bodies suitable for use with the liquid dispensing apparatus 102 include, without limitation, the pipette body of an Eppendorf Reference® 2 manual pipette, sold by Eppendorf AG, Germany.

The pipette tip 404 is removably connected to a second, lower end 522 of the piston housing 506, and defines an interior volume 408 that is in fluid communication with the piston chamber 504. The pipette tip 404 includes a first, connection end 410 connected to the lower end 522 of the piston housing 506, and a second end 412 distal from the first end 410 that defines an opening 414 through which liquids are aspirated and/or dispensed. In the example embodiment, the pipette tip 404 is conically shaped such that the cross-section of the pipette tip 404 gradually and continuously decreases from the first end 410 to the second end 412 of the pipette tip 404. In some embodiments, the pipette tip 404 is designed to be disposed following one or more liquid transfer processes described herein.

The pipette body 402 and/or the pipette tip 404 may be interchanged with other pipette bodies and pipette tips to vary the dispensing capacity of the liquid dispensing apparatus 102. In some embodiments, for example, the capacities of pipette body 402 and the pipette tip 404 are such that the liquid dispensing apparatus 102 can be set (e.g., using the controller 106) to accurately deliver (i.e., aspirate and/or dispense with a single piston stroke) liquid volumes from 100 μL up to 5,000 μL, such as from 500 μL up to 5,000 μL. In other embodiments, the capacities of pipette body 402 and the pipette tip 404 are such that the liquid dispensing apparatus 102 can be set to deliver liquid volumes as low as 0.1 μL and as high as 10 mL.

The linear actuator 406 is connected to the pipette body 402, and is configured to control linear displacement of the piston 502 within the piston chamber 504 to control a volume of liquid aspirated and/or dispensed by pipette assembly 202. In the example embodiment, the linear actuator 406 includes a third stepper motor 416 that drives a rod 602 (shown in FIG. 6) along a linear path via a linkage mechanism (not shown) that converts rotational motion of the motor into linear motion. Suitable linkage mechanisms for connecting the third stepper motor 416 to the rod 602 include, for example and without limitation, rack and pinion assemblies and leadscrew assemblies. The third stepper motor 416 may have any suitable stepper motor configuration that enables the liquid dispensing apparatus 102 to function as described herein. For example, the third stepper motor 416 may have the same configuration as the first stepper motor 110 and/or the second stepper motor 112.

Figure 6:
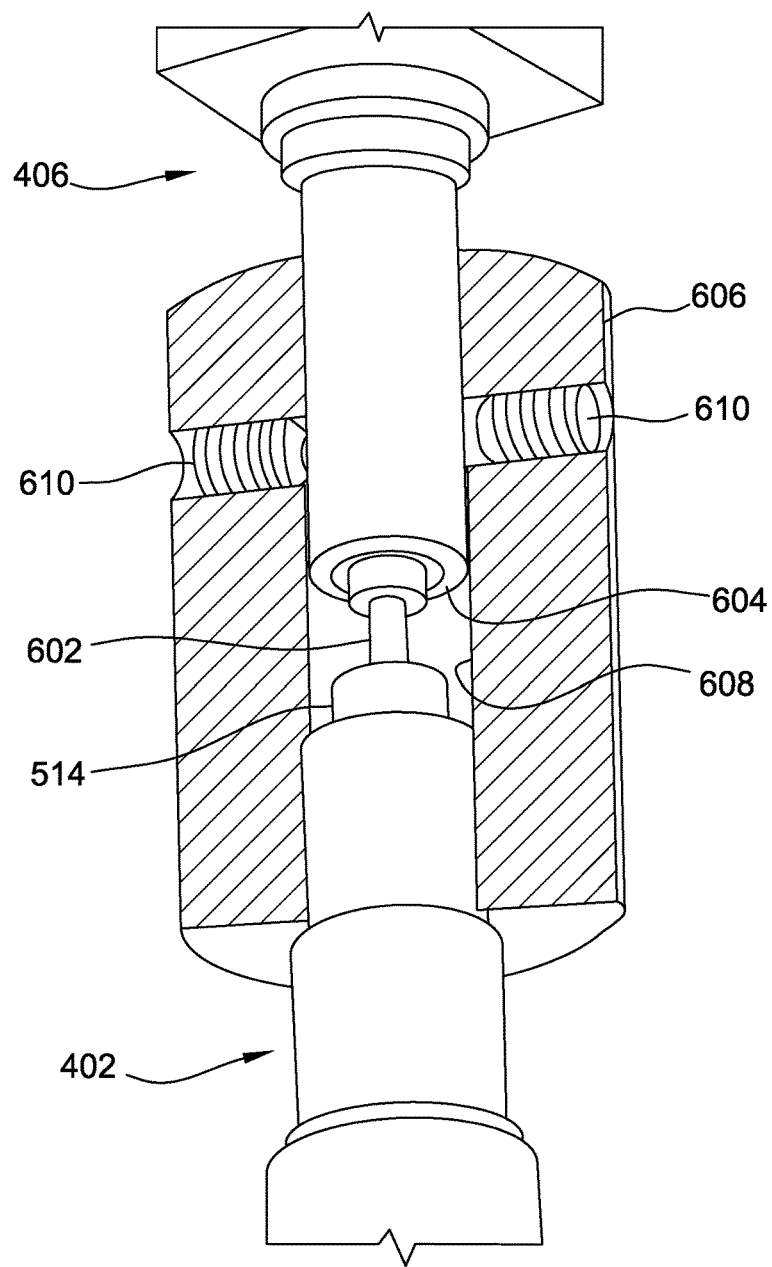
FIG. 6 is an enlarged view of a portion of the pipette assembly shown in FIG. 4.

The linear actuator 406 is operatively connected to the piston 502 by the rod 602. In particular, as shown in FIG. 6, the rod 602 protrudes from a lower end 604 of the linear actuator 406 and engages the piston mount 514. Operation of the third stepper motor 416 causes the rod 602 to move linearly upward or downward, and to linearly displace the piston mount 514 and the piston 502. This in turn causes the piston 502 to create a positive or negative pressure differential within the piston chamber 504, allowing liquids to be dispensed or aspirated, respectively, through the pipette tip opening 414.

In the illustrated embodiment, the pipette assembly 202 also includes a connector 606 to connect the pipette body 402 with the linear actuator 406, and to align the piston 502 of the pipette body 402 with the linear actuator rod 602. The connector 606 has a cylindrical opening 608 defined therein that extends from a top of the connector 606 to a bottom of the connector 606. A portion of the linear actuator 406 is positioned within the cylindrical opening 608 at the top of the connector 606 and is secured to the connector 606 by suitable connection means. In the illustrated embodiment, the connector 606 is connected to the linear actuator 406 by a pair of diametrically opposed set screws 610 that extend through the sides of the connector 606 and engage the linear actuator 406 within the cylindrical opening 608. A portion of the pipette body 402 is received in the cylindrical opening 608 at the bottom of the connector 606 to connect the pipette body 402 to the connector 606. In some embodiments, the pipette body 402 is removably connected to the connector 606 such that the pipette body 402 can be interchanged with other pipette bodies having different configurations (e.g., different volumes). Suitable means for removably connecting the pipette body 402 to the connector 606 include, for example and without limitation, one or more detents, a bayonet connection, and a threaded connection.

In the illustrated embodiment, the pipette assembly 202 also includes a pipette tip retaining clip 418 (shown in FIG. 4) to maintain the connection between the pipette body 402 and the pipette tip 404. The retaining clip 418 inhibits the pipette tip 404 from being unintentionally dislodged or otherwise disconnected from the pipette body 402 during operation. In the example embodiment, the retaining clip 418 is positioned at the second end 522 of the piston housing 506 (shown in FIG. 5), and applies a clamping force to the pipette tip 404 against the second end 522 of the piston housing 506.

Figure 7:
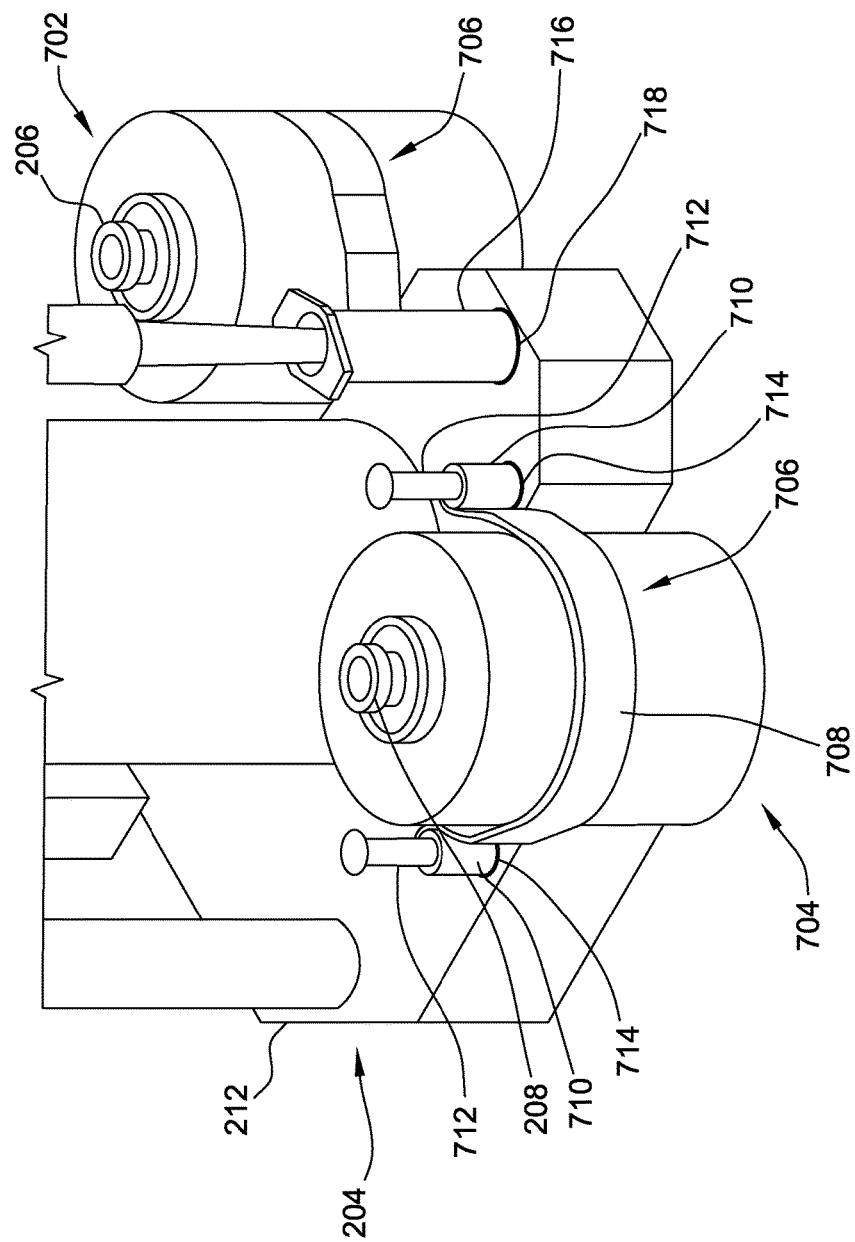
FIG. 7 is a perspective view of two vial assemblies included in the liquid dispensing apparatus shown in FIG. 2.
Figure 8:
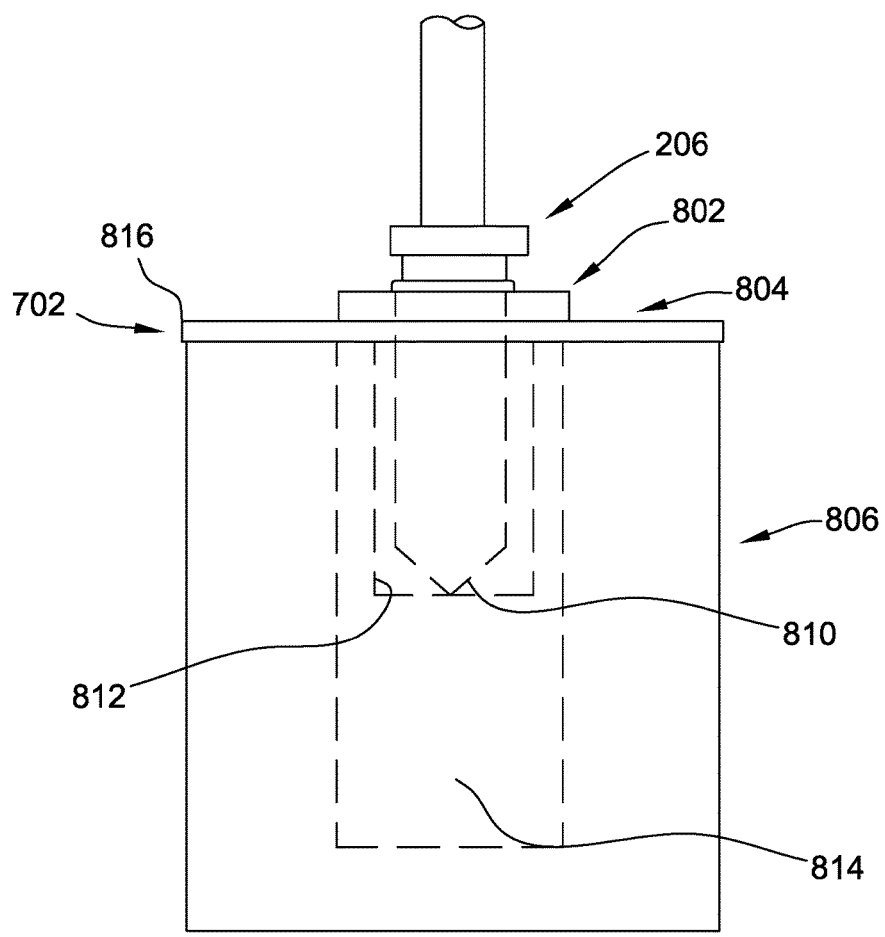
FIG. 8 is a side view of one of the vial assemblies shown in FIG. 7.

Referring to FIGS. 7 and 8, the source vial 206 and the destination vial 208 are housed within a source vial assembly 702 and a destination vial assembly 704, respectively. As shown in FIG. 8, the source vial assembly 702 includes the source vial 206, a vial holder 802, a liquid retaining disc 804, and a radiation shield 806 that at least partially encloses the source vial 206, the vial holder 802, and the liquid retaining disc 804.

In the example embodiment, the source vial 206 is constructed of glass. In other embodiments, the source vial 206 may be constructed from materials other than glass. Further, in the example embodiment, the source vial 206 is a conical-bottom vial. That is, the source vial 206 has a conically-shaped bottom 810. The use of vials having conically-shaped bottoms facilitates transferring liquids through the liquid dispensing apparatus 102 by facilitating removal of nearly all liquid from the vial while preventing occlusion of the pipette tip opening 414 during aspiration.

The vial holder 802 defines a vial chamber 812 in which the source vial 206 is positioned. The vial holder 802 has a leak-tight construction to prevent or inhibit liquids from leaking out of the vial holder 802. Suitable materials from which the vial holder 802 may be constructed include, for example and without limitation, polyactic acid (PLA). In some embodiments, each vial holder 802 is designed for use with a specific vial such that the bottom 810 of the vial, when positioned within the vial holder 802, is positioned at a predetermined height relative to another component of the liquid dispensing apparatus 102, such as the base 212 or the pipette tip 404. In one embodiment, for example, each vial holder 802 includes a spacer 814 that positions the bottom of the vial at a predetermined height relative to the pipette tip 404 when the pipette tip 404 is in a fully lowered position. Further, in some embodiments, the vials 206, 208 and/or the vial holders 802 may be interchanged with other vials and vial holders to maintain the bottom of the vials at a consistent height.

The liquid retaining disc 804 is connected proximate the top of the vial holder 802, and extends radially outward therefrom to an annular lip 816. The lip 816 extends upward to retain liquids on the liquid retaining disc 804. In some embodiments, the liquid retaining disc 804 is configured to contain up to 5 mL of liquid. Suitable materials from which the liquid retaining disc 804 may be constructed include, for example and without limitation, polyurethane.

The radiation shield 806 is constructed of suitable radiation shielding material, including, for example and without limitation, lead, depleted uranium, and tungsten. In the example embodiment, the radiation shield 806 is a cylinder having a closed bottom end and an open top end in which the vial holder 802 and liquid retaining disc 804 are received. In other embodiments, the radiation shield 806 may have any suitable configuration that enables the liquid dispensing apparatus 102 to function as described herein.

Although not shown in FIG. 8, the destination vial assembly 704 has the same construction and configuration as the source vial assembly 702. For example, the destination vial assembly 704 includes a vial (i.e., the destination vial 208), a vial holder, a liquid retaining disc, and a radiation shield.

In the illustrated embodiment, the source vial assembly 702 and the destination vial assembly 704 are secured to the support frame 204 by a bracket or brace 706. In the example embodiment, each of the source vial assembly 702 and the destination vial assembly 704 are secured to the base 212 of the support frame 204 by a respective brace 706. In the example embodiment, each brace 706 includes a band 708 shaped complementary to the outer contour of a corresponding vial assembly. The band 708 includes a pin collar 710 disposed at each end of the band 708. Each pin collar 710 is sized and shaped to receive a pin 712 therein. The band 708 has a suitable length and shape such that the pin collars 710 are positioned relative to one another so as to simultaneously align with respective pin holes 714 defined by the support frame base 212. A pin 712 extends through each collar 710 and its associated pin hole 714 to secure the brace 706 to the support frame 204, and thereby secure a corresponding vial assembly to the support frame 204. In some embodiments, the band 708 has a rigid construction such that the band 708 maintains its general shape in the absence of an applied force. That is, the band 708 does not bow or sag under its own weight. In some embodiments, for example, the band 708 is constructed from metal or rigid plastic. Further, in some embodiments, components of the brace 706 may be formed as a single, integral unit. In some embodiments, for example, the band 708, pin collars 710, and pins 712 are formed as a single, integral unit (e.g., from welded stainless steel).

In the example embodiment, the support frame 204 also includes a pipette tip receptacle 716 connected to the base 212. In example embodiment, the pipette tip receptacle 716 is a 20 mL syringe barrel removably connected to the base 212. In some embodiments, the pipette tip receptacle 716 may be sealed (e.g., with a luer plug) to retain liquid spills. Further, in some embodiments, the pipette tip 404 may be positioned within the pipette tip receptacle 716 between liquid transferring processes. In the example embodiment, the pipette tip receptacle 716 is located between the source vial 206 and the destination vial 208, and extends at least partially into a hole 718 defined by the base 212. The pipette tip receptacle 716 may be removed from the hole 718 and discarded using, for example, telemanipulators. Further, in some embodiments, the pipette tip 404 may be ejected (i.e., disconnected) from the pipette body 402 into the pipette tip receptacle 716 to facilitate disposal of the pipette tip 404 while controlling contamination that might be present on the pipette tip exterior.

In some embodiments, the liquid dispensing apparatus 102 does not include any (i.e., is free of) radiation-sensitive electronics. In some embodiments, for example, each of the stepper motors 110, 112, 416 contains no electronics, and control is achieved by adjusting stator current via the controller 106 (e.g., via stepper drives) located outside the radiation containment chamber 104. In such embodiments, the stepper motors 110, 112, 416 do not include any position sensors or feedback sensors or devices, such as encoders, that are sensitive to radiation. As used herein, the term radiation-sensitive electronics refers to electronic components, such as sensors, that are susceptible to damage, reduced performance, or reduced functionality resulting from exposure to nuclear radiation (e.g., gamma and beta radiation). Examples of radiation-sensitive electronics include, but are not limited to, encoders, optical sensors (e.g., fiber optic sensors, reflective light sensors, photo-optic sensors), proximity sensors (e.g., capacitive or inductive based sensors), and processors.

The absence of radiation-sensitive electronics, such as those used in other liquid handling systems, facilitates operation of the liquid dispensing apparatus 102 in high radiation environments. In some embodiments, for example, the liquid dispensing apparatus 102 is capable of operating for extended periods of time in a high radiation environment, such as within the radiation containment chamber 104. In some embodiments, for example, the liquid dispensing apparatus 102 is capable of operating within a high radiation area and even a very high radiation area for at least 10 cumulative hours, for at least 20 cumulative hours, for at least 30 cumulative hours, for at least 50 cumulative hours, for at least 100 cumulative hours, for at least 200 cumulative hours, for at least 300 cumulative hours, for at least 500 cumulative hours, and even up to 1,000 cumulative hours.

As used herein, the term "high radiation area" means an area in which radiation levels from radiation sources external to an individual's body would result in an individual receiving a dose equivalent in excess of 0.1 rem (1 mSv) in 1 hour at 30 centimeters from the radiation source or 30 centimeters from any surface that the radiation penetrates. As used herein, the term "very high radiation area" means an area in which radiation levels from radiation sources external to an individual's body would result in an individual receiving an absorbed dose in excess of 500 rads (5 grays) in 1 hour at 1 meter from a radiation source or 1 meter from any surface that the radiation penetrates.

Further, in some embodiments, the liquid dispensing apparatus 102 is capable of operating in a radioactive field equal to 5 million millirem per hour (mrem/hr) for at least 10 cumulative hours, for at least 20 cumulative hours, for at least 30 cumulative hours, for at least 50 cumulative hours, for at least 100 cumulative hours, for at least 200 cumulative hours, for at least 300 cumulative hours, for at least 500 cumulative hours, and even up to 1,000 cumulative hours.

In some embodiments, the liquid dispensing apparatus 102 includes one or more mechanical switches that provide an indication of the position of the pipette assembly 202 relative to the support frame 204. Suitable mechanical switches include, for example and without limitation, electrical contacts that complete or close an electrical circuit when the contacts are engaged. In this embodiment, the liquid dispensing apparatus 102 includes a first mechanical switch 420 (shown in FIG. 4) and a second mechanical switch 228 (shown in FIG. 2). The first mechanical switch 420 is located proximate the linear actuator 406, and is activated or switched (e.g., electrical contacts are engaged with one another) when the linear actuator rod 602 is in a fully retracted position. The second mechanical switch 228 is located between the support arm 216 and the top of the column 214, and diametrically opposite to the pipette tip receptacle 716. The second mechanical switch 228 is activated or switched when the pipette assembly 202 is in a fully lowered position. The first and second mechanical switches 420 and 228 are connected to the controller 106. The controller 106 may determine whether one or more operations should or should not be performed based on the status of the first mechanical switch 420 and/or the second mechanical switch 228. For example, the controller 106 may determine that an aspiration or dispense operation should not be performed when the second mechanical switch 228 is activated.

As noted above, the controller 106 is connected to the liquid dispensing apparatus 102 to control operation thereof. In particular, the controller 106 is connected to each of the first stepper motor 110, the second stepper motor 112, and the third stepper motor 416 to output control signals to each of the motors and control operation thereof. In some embodiments, the controller 106 includes or is connected to the stepper motors 110, 112, 416 through one or more suitable stepper drivers configured to output and/or regulate the supply of current supplied to the stepper motors. In some embodiments, for example, control signals generated by the controller 106 are translated or converted into a suitable current waveform by a stepper driver to achieve a desired number of motor steps.

Figure 9:
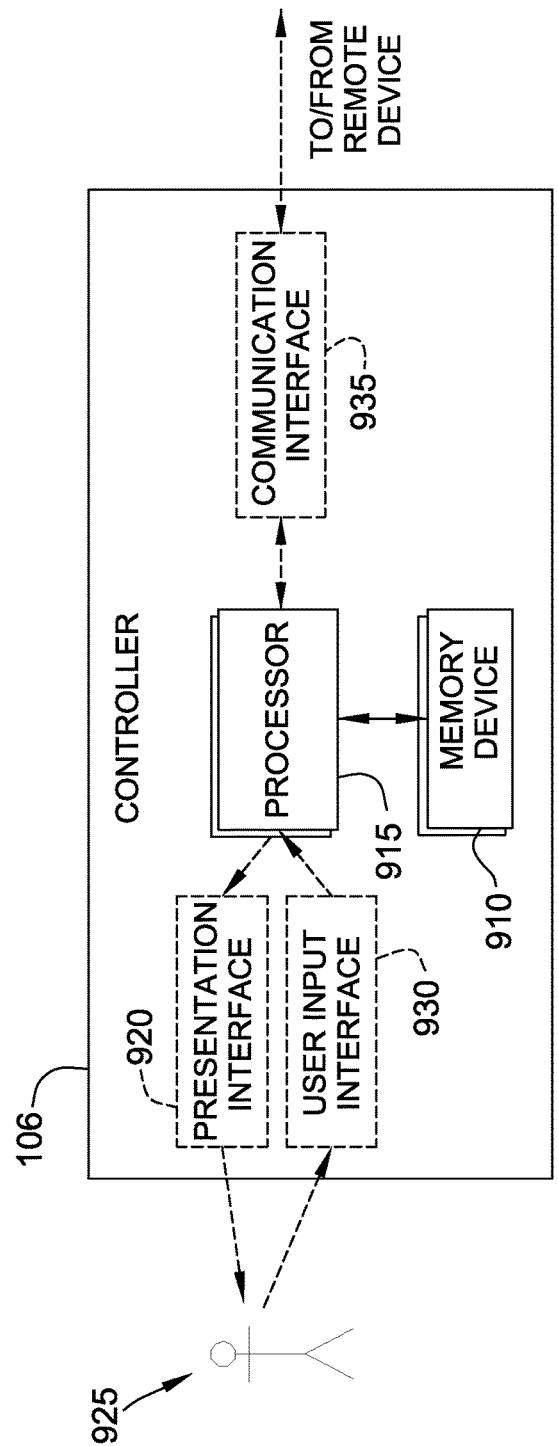
FIG. 9 is a block diagram of a controller included in the system of FIG. 1.

FIG. 9 is a block diagram of the controller 106. The controller 106 includes at least one memory device 910 and a processor 915 that is coupled to the memory device 910 for executing instructions. In this embodiment, executable instructions are stored in the memory device 910, and the controller 106 performs one or more operations described herein by programming the processor 915. For example, the processor 915 may be programmed by encoding an operation as one or more executable instructions and by providing the executable instructions in the memory device 910.

The processor 915 may include one or more processing units (e.g., in a multi-core configuration). Further, the processor 915 may be implemented using one or more heterogeneous processor systems in which a main processor is present with secondary processors on a single chip. As another illustrative example, the processor 915 may be a symmetric multi-processor system containing multiple processors of the same type. Further, the processor 915 may be implemented using any suitable programmable circuit including one or more systems and microcontrollers, microprocessors, programmable logic controllers (PLCs), reduced instruction set circuits (RISC), application specific integrated circuits (ASIC), programmable logic circuits, field programmable gate arrays (FPGA), and any other circuit capable of executing the functions described herein. In this embodiment, the processor 915 controls operation of liquid dispensing apparatus 102 by outputting control signals to each of the first, second, and third stepper motors 110, 112, 416.

The memory device 910 is one or more devices that enable information such as executable instructions and/or other data to be stored and retrieved. The memory device 910 may include one or more computer readable media, such as, without limitation, dynamic random access memory (DRAM), static random access memory (SRAM), a solid state disk, and/or a hard disk. The memory device 910 may be configured to store, without limitation, application source code, application object code, source code portions of interest, object code portions of interest, configuration data, execution events and/or any other type of data.

In this embodiment, the controller 106 includes a presentation interface 920 that is connected to the processor 915. The presentation interface 920 presents information, such as application source code and/or execution events, to a user 925, such as a technician or operator. For example, the presentation interface 920 may include a display adapter (not shown) that may be coupled to a display device, such as a cathode ray tube (CRT), a liquid crystal display (LCD), an organic LED (OLED) display, and/or an "electronic ink" display. The presentation interface 920 may include one or more display devices. In this embodiment, the presentation interface 920 displays a graphical user interface for receiving information from the user 925, such as a target dispense or transfer volume.

The controller 106 also includes a user input interface 930 in this embodiment. The user input interface 930 is connected to the processor 915 and receives input from the user 925. The user input interface 930 may include, for example, a keyboard, a pointing device, a mouse, a stylus, a touch sensitive panel (e.g., a touch pad or a touch screen), a gyroscope, an accelerometer, a position detector, and/or an audio user input interface. A single component, such as a touch screen, may function as both a display device of the presentation interface 920 and the user input interface 930. In this embodiment, the user input interface 930 receives an input associated with a target transfer volume of liquid to be transferred from the source vial 206 to the destination vial 208 including, for example and without limitation, a volume of liquid in milliliters. The presentation interface 920 and the user input interface 930 may be collectively referred to as an operator interface or a human-machine interface (HMI).

In this embodiment, the controller 106 further includes a communication interface 935 connected to the processor 915. The communication interface 935 communicates with one or more remote devices, such as the liquid dispensing apparatus 102.

In operation, the liquid dispensing apparatus 102 transfers radioactive liquid from the source vial 206 to the destination vial 208 in response to control signals received from the controller 106. Specifically, in this embodiment, the controller 106 (specifically, the processor 915) receives an input (e.g., from the user 925 via the user input interface 930) associated with a target transfer volume to be transferred from the source vial 206 to the destination vial 208. The controller 106 controls operation of the first stepper motor 110 and the second stepper motor 112 (e.g., by controlling the supply of current to the first and second stepper motors 110, 112) to position the pipette assembly 202 over the source vial 206, and to the lower the pipette assembly 202 such that the pipette tip 404 is submerged in radioactive liquid within the source vial 206.

Specifically, in this embodiment, the controller 106 determines a number of steps by which each of the first stepper motor 110 and the second stepper motor 112 need to be rotated to position the pipette assembly 202 in a position in which the pipette tip 404 is submerged in radioactive liquid within the source vial 206, also referred to as an aspiration position. The controller 106 may determine the number of steps, for example, by determining a difference in height and rotational position between a current position of the pipette assembly 202 and the desired aspiration position. Based on the differences in height and rotational position, the controller 106 may determine the number of steps using look-up tables, formulas, algorithms, or other instructions (e.g., stored in the memory device 910) that correlate a motor step of the first stepper motor 110 to an incremental rotational distance, and a motor step of the second stepper motor 112 to an incremental vertical distance. In some embodiments, the controller 106 determines a difference in height and/or rotational position of the current position of the pipette assembly 202 and a desired position of the pipette assembly 202 (e.g., an aspiration or dispense position) by tracking or logging the position of the pipette assembly 202 based on previous control signals output to the first stepper motor 110, the second stepper motor 112, and/or the third stepper motor 416.

Additionally, in this embodiment, the controller 106 outputs a control signal to each of the first stepper motor 110 and the second stepper motor 112 based on the determined number of steps. The control signal may be output as or converted to (e.g., by a stepper drive) a current waveform that energizes the windings of the stepper motors in a desired sequence and a desired number of times that corresponds to the determined number of steps. In response to the control signals, the first stepper motor 110 and the second stepper motor 112 rotate, thereby rotating and vertically displacing, respectively, the support arm 216 such that the pipette assembly 202 is positioned in the desired position.

In this embodiment, the controller 106 also controls operation of the linear actuator 406 via the third stepper motor 416 (e.g., by controlling the supply of current to the third stepper motor 416) to control aspiration and dispensing operations. Specifically, in this embodiment, the controller 106 determines, based on an input associated with a target transfer volume, a number of steps by which the third stepper motor 416 needs to be rotated to displace the piston 502 a distance that results in the target transfer volume being aspirated and/or dispensed by the pipette assembly 202. The controller 106 (specifically, the processor 915) may determine the number of steps for the third stepper motor 416, for example, using look-up tables, formulas, algorithms, or other instructions (e.g., stored in the memory device 910) that correlate a number of steps of the third stepper motor 416 to a resulting piston displacement and/or a volume of liquid aspirated or dispensed by the pipette assembly 202.

Additionally, in this embodiment, the controller 106 outputs a control signal to the third stepper motor 416 based on the determined number of steps. The control signal may be output as or converted to (e.g., by a stepper drive) a current waveform that energizes the windings of the third stepper motor 416 in a desired sequence and a desired number of times that corresponds to the determined number of steps. In response to the control signals, the third stepper motor 416 rotates, causing actuation of the linear actuator 406 and displacement of the rod 602 and the piston 502. Displacement of the piston 502 generates a positive or negative pressure differential within the piston chamber 504, resulting in liquid being aspirated or dispensed from the pipette tip 404.

Following aspiration, the controller 106 controls operation of the first stepper motor 110, the second stepper motor 112, and the third stepper motor 416 to position the pipette assembly 202 over the destination vial 208 and dispense the target transfer volume into the destination vial 208. The controller 106 may control the first, second, and third stepper motors 110, 112, 416 in the same manner described above with reference to the aspiration procedure.

In some embodiments, the pipette body 402 and/or the pipette tip 404 may exhibit a non-linear response or relationship between the number of steps by which the third stepper motor 416 is rotated and the volume of liquid aspirated or dispensed by the pipette assembly 202 over the full usable dispensing range (i.e., capacity) of the pipette assembly 202. In such embodiments, discrete volume ranges may be identified and stored in the controller 106 (specifically, in the memory device 910), and different factors, coefficients, formulas, and/or algorithms may be assigned to each range to facilitate determining the number of steps by which the third stepper motor 416 needs to be rotated to achieve target liquid volumes across the entire dispensing range of the pipette assembly 202. In some embodiments, for example, the controller 106 determines separate equations, such as linear equations, for discrete segments of a target dispense volume/motor steps curve.

Figure 10:
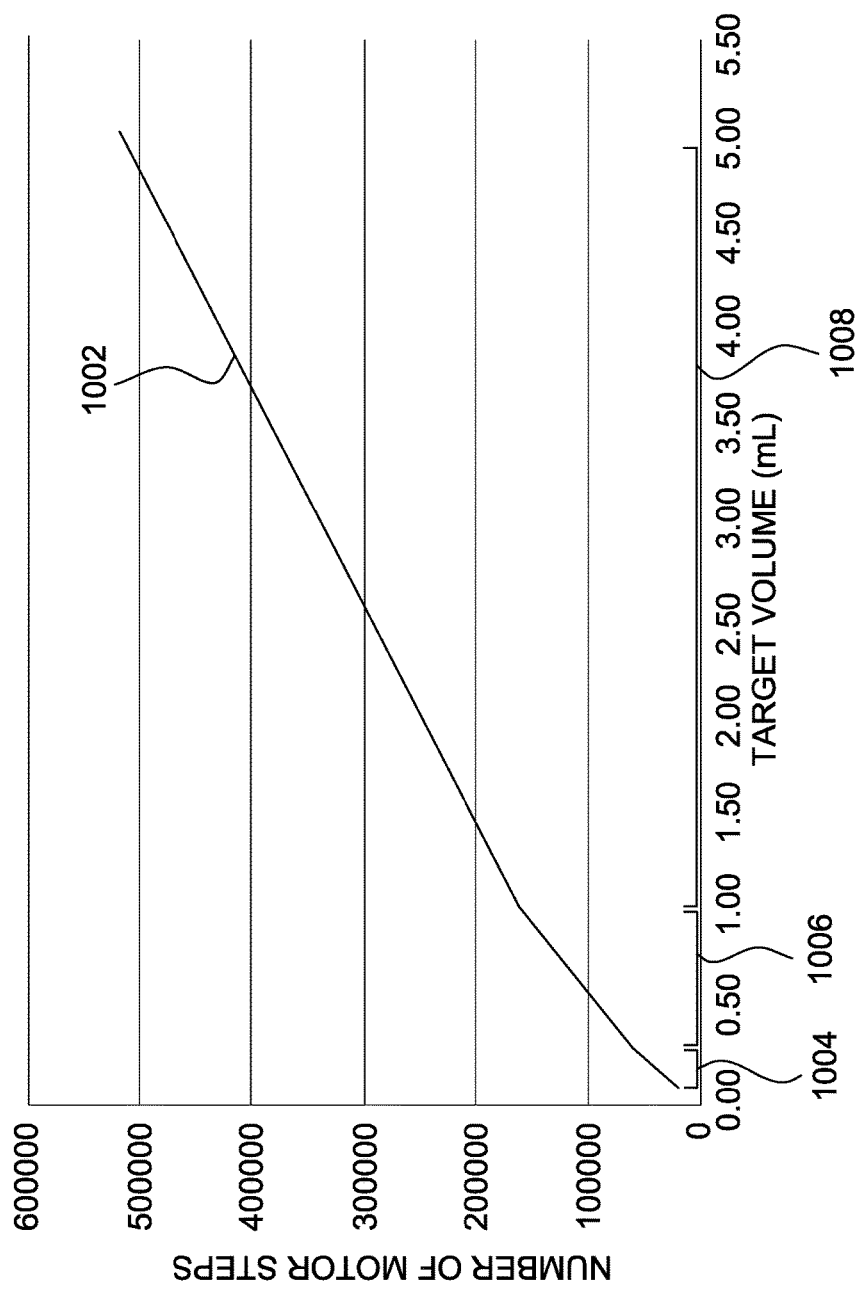
FIG. 10 is a plot of an example target transfer volume/motor steps curve for the pipette assembly shown in FIG. 4.

FIG. 10 is a plot of an example target transfer volume/motor steps curve 1002 for the pipette assembly 202. The curve 1002 illustrates an example relationship between the target transfer volume for the pipette assembly 202 and the corresponding number of steps for third stepper motor 416 needed to aspirate or dispense the target transfer volume. As shown in FIG. 10, the curve 1002 includes three discrete volume ranges: a first volume range 1004 from 0.1 to 0.3 mL, a second volume range 1006 from 0.3 mL to 1.0 mL, and a third volume range 1008 from 1.0 mL to 5.0 mL. The curve 1002 may be stored in the controller 106 (specifically, in the memory device 910), and/or the controller 106 (specifically, the processor 915) may determine different equations or algorithms for each of the volume ranges 1004, 1006, 1008 to determine the number of steps by which the third stepper motor 416 should be rotated. In this embodiment, for example, the controller 106 determines a different linear equation for each of the first volume range 1004, the second volume range 1006, and the third volume range 1008, and uses the linear equations in combination with an input target transfer volume to determine the number of steps by which the third stepper motor 416 should be rotated to achieve the target transfer volume.

Accounting for the non-linear response of the pipette assembly 202 as described herein facilitates accurately aspirating and dispensing target transfer volumes over the full usable dispensing range (i.e., capacity) of the pipette assembly 202. In some embodiments, for example, the liquid dispensing apparatus 102 is capable of dispensing liquid with a single piston stroke over a range of 100 µL to 5,000 µL within +/−5.0% of a target dispense volume, within +/−3.0% of a target dispense volume, within +/−2.5% of a target dispense volume, within +/−2.0% of a target dispense volume, within +/−1.5% of a target dispense volume, and even within +/−1.0% of a target dispense volume. Additionally, in some embodiments, the liquid dispensing apparatus 102 is capable of dispensing liquid with a single piston stroke within +/−1.0% of a target volume over a range of 500 µL to 5,000 µL, over a range of 300 µL to 5,000 µL, over a range of 200 µL to 5,000 µL, and even over a range of 100 µL to 5,000 µL.

In some embodiments, the controller 106 further controls the liquid dispensing apparatus 102 (e.g., by controlling the supply of current to each of the stepper motors 110, 112, 416) to reduce or minimize errors in liquid dispensing and facilitate more accurate, precise dispense volumes. In some embodiments, for example, the controller 106 controls the height of the pipette tip 404 relative to the bottom of the source vial 206 during aspiration to maintain spacing between the pipette tip 404 and the bottom of the source vial 206. This facilitates preventing occlusion of the pipette tip opening 414 during aspiration, which might otherwise result in errors in the volume of liquid aspirated. The controller 106 controls the height of the pipette tip 404 by controlling the supply of current to the second stepper motor 112, which adjusts the height of the support arm 216 and, consequently, the pipette assembly 202.

Additionally, in some embodiments, the controller 106 controls the height of the pipette tip 404 to aspirate a target volume of liquid by performing a plurality of partial aspirations at different elevations or depths within the source vial 206.

In one embodiment, for example, the controller is configured to control the second stepper motor 112 to position the pipette tip 404 at a first height, to control the third stepper motor 416 to displace the piston 502 and aspirate a first volume of radioactive liquid from the source vial 206 while the pipette tip 404 is positioned at the first height, to further control the second stepper motor 112 to position the pipette tip 404 at a second height lower than the first height, and to further control the third stepper motor 416 to displace the piston 502 and aspirate a second volume of radioactive liquid from the source vial 206 while the pipette tip 404 is positioned at the second height.

Performing partial aspirations at multiple different heights or submersion depths within the source vial 206 facilitates preventing liquid overflows from the source vial 206 that might otherwise occur if the pipette tip 404 were moved directly to the bottom of the source vial 206 at the beginning of aspiration. Additionally, performing partial aspirations at different heights facilitates reducing or minimizing the amount of liquid forced into the pipette tip 404 during submersion by limiting the submersion depth of the pipette tip and the resulting pressure differential across the pipette tip opening 414.

In some embodiments, the controller 106 also controls the aspiration rate of the pipette assembly 202 at a slow, steady aspiration rate to ensure the entire target volume is aspirated with minimal turbulence. For example, the controller 106 may control the rate of piston displacement during aspiration by controlling the supply of current to the third stepper motor 416, which controls the speed of the third stepper motor 416 and, consequently, the rate of piston displacement. In some embodiments, for example, the controller 106 controls the rate of piston displacement at a displacement rate of between 7 seconds to 10 seconds per full piston stroke.

Additionally, in some embodiments, the controller 106 controls removal of the pipette tip 404 from the source vial 206 to reduce or minimize errors in liquid dispensing. In some embodiments, for example, the controller 106 maintains the pipette tip 404 within the source vial 206 for a predetermined or preset delay time following aspiration to ensure aspiration is complete prior to withdrawing the pipette tip 404 from the source vial 206. Suitable delay times following aspiration include, for example and without limitation 1 second, 2 seconds, 3 seconds, 5 seconds, and 10 seconds. In some embodiments, the controller 106 also controls the rate at which the pipette tip 404 is withdrawn from the liquid within the source vial 206 by controlling the supply of current to the second stepper motor 112. In some embodiments, for example, the controller 106 removes or withdraws the pipette tip 404 from the source vial 206 following aspiration at a rate of about 4 seconds from a fully lowered position to a fully raised position. Controlling the rate at which the pipette tip 404 is removed from the source vial liquid allows surface tension of the liquid to eliminate or reduce liquid pooling on the outside of the pipette tip 404, which might otherwise drip down and be dispensed with the liquid inside the pipette tip 404.

In some embodiments, the controller 106 also controls insertion of the pipette tip 404 into the destination vial 208 to reduce or minimize errors in liquid dispensing. In some embodiments, for example, the controller 106 lowers the pipette tip 404 below the opening of the destination vial 208 prior to dispensing any liquid to prevent or inhibit liquid from being dispensed outside the destination vial 208.

Additionally, in some embodiments, the controller 106 controls the piston displacement rate during liquid dispensing into the destination vial 208 to facilitate the use of surface tension to eliminate liquid pooling on the inside of the pipette tip 404 walls. Specifically, in some embodiments, the controller 106 decelerates the piston 502 near the end of a liquid dispensing process (e.g., by controlling the supply of current to the third stepper motor 416).

Additionally, in some embodiments, if an incomplete dispense condition is detected, the controller 106 automatically flushes liquid within the pipette tip 404 back into the source vial 206, and then automatically wets the interior surface of the pipette tip 404 to eliminate interior surface drops that might otherwise increase subsequent dispensing error.

Embodiments of the systems and methods described herein provide several advantages over known liquid handling systems. In particular, embodiments of the systems and methods facilitate accurately transferring precise amounts of radioactive liquid between a source vial and a destination vial, while avoiding or minimizing operator exposure to nuclear radiation. For example, embodiments of the systems and methods described herein use a pipette assembly to transfer liquid between the source vial and the destination vial. Use of a pipette assembly to aspirate and dispense liquids provides several advantages over other liquid transfer mechanisms, such as peristaltic, syringe, or rotary piston pumps. For example, virtually no liquid is lost in the pipetting process because there are no tubes or other lines in which the liquid may otherwise collect or be trapped. Additionally, no pump calibration is required, thereby avoiding time, effort, and measurement instrumentation complexity (e.g. weight measurement) associated with peristaltic pump calibration. Further, unlike rotary piston pumps, the pipette tips used in pipette assemblies can be pre-sterilized and disposed with each use to minimize contamination and cross-contamination between batches.

Additionally, embodiments of the liquid dispensing apparatus described herein facilitate the use of pipette assemblies to transfer liquids, while avoiding drawbacks commonly associated with the use of pipettes, such as variation in operator pipetting technique, which can adversely affect dispensing precision and accuracy. Examples of variation in pipetting technique include pipette tip angle, pipette aspiration volume, speed of pipette aspiration, duration of pause after aspiration, speed of pipette withdrawal from liquid, dispense speed, and completion of blow-out without tip ejection. Additionally, manual dispensing requires physical access to the equipment, which may result in operator exposure to radioactive environments.

EXAMPLE

Experimental testing was conducted on a liquid dispensing apparatus having substantially the same configuration as the liquid dispensing apparatus 102. The experimental testing included five different test runs. In each test run, 20 different target dispense volumes were assigned to the liquid dispensing apparatus ranging from 0.1 mL to 5.0 mL. Under the control of a controller, such as the controller 106, the liquid dispensing apparatus transferred 20 different liquid volumes from a source vial to a destination volume based on the target dispense volumes. The first test run was conducted without wetting the inside of the pipette tip. In the second test run, the interior of the pipette tip was wetted prior to liquid being transferred with the pipette tip. Following the second test run, the pipette tip was replaced with another pipette tip having substantially the same configuration. The pipette tip was not wetted in the third test run, and the pipette tip was wetted in the fourth test run. Following the fourth test run, the pipette body was replaced with a pipette body having substantially the same configuration. The fifth test run was then carried out with the new pipette body by wetting the pipette tip prior to liquid being transferred with the pipette tip. Each test run was performed using the pipette body from an Eppendorf Reference® 2 manual pipette and a pipette tip having a capacity rating of 0.5 mL to 5.0 mL. Following completion of the test runs, the actual dispense volumes were compared to the target dispense volumes, and percentage differences were calculated for each target dispense volume. The results of test runs 1-4 are listed below in Table 1, and the results of test run 5 are listed below in Table 2.

TABLE 1

Results of Test runs 1-4

| Target Dispense Volume (mL) | First Test Run | % Diff | Second Test Run | % Diff | Third Test Run | % Diff | Fourth Test Run | % Diff |
|---|---|---|---|---|---|---|---|---|
| 0.100 | 0.102 | 2.00% | 0.103 | 3.00% | 0.101 | 1.00% | 0.099 | −1.00% |
| 0.200 | 0.200 | 0.00% | 0.2 | 0.00% | 0.197 | −1.50% | 0.2 | 0.00% |
| 0.300 | 0.302 | 0.67% | 0.303 | 1.00% | 0.301 | 0.33% | 0.295 | −1.67% |
| 0.400 | 0.402 | 0.50% | 0.398 | −0.50% | 0.394 | −1.50% | 0.399 | −0.25% |
| 0.500 | 0.496 | −0.80% | 0.501 | 0.20% | 0.495 | −1.00% | 0.497 | −0.60% |
| 0.600 | 0.592 | −1.33% | 0.597 | −0.50% | 0.596 | −0.67% | 0.596 | −0.67% |
| 0.750 | 0.745 | −0.67% | 0.745 | −0.67% | 0.745 | −0.67% | 0.745 | −0.67% |
| 0.900 | 0.896 | −0.44% | 0.898 | −0.22% | 0.896 | −0.44% | 0.897 | −0.33% |
| 1.000 | 0.999 | −0.10% | 0.994 | −0.60% | 0.99 | −1.00% | 0.997 | −0.30% |
| 1.100 | 1.089 | −1.00% | 1.092 | −0.73% | 1.095 | −0.45% | 1.098 | −0.18% |
| 1.250 | 1.243 | −0.56% | 1.248 | −0.16% | 1.24 | −0.80% | 1.247 | −0.24% |
| 1.500 | 1.489 | −0.73% | 1.496 | −0.27% | 1.491 | −0.60% | 1.492 | −0.53% |
| 2.000 | 1.992 | −0.40% | 1.997 | −0.15% | 1.991 | −0.45% | 1.992 | −0.40% |
| 3.000 | 2.983 | −0.57% | 2.985 | −0.50% | 2.984 | −0.53% | 2.987 | −0.43% |
| 4.000 | 3.979 | −0.52% | 3.985 | −0.38% | 3.977 | −0.58% | 3.988 | −0.30% |
| 4.250 | 4.230 | −0.47% | 4.231 | −0.45% | 4.235 | −0.35% | 4.233 | −0.40% |
| 4.500 | 4.484 | −0.36% | 4.491 | −0.20% | 4.483 | −0.38% | 4.489 | −0.24% |

TABLE 1-continued

Results of Test runs 1-4

| Target Dispense Volume (mL) | First Test Run | % Diff | Second Test Run | % Diff | Third Test Run | % Diff | Fourth Test Run | % Diff |
|---|---|---|---|---|---|---|---|---|
| 4.750 | 4.726 | −0.51% | 4.736 | −0.29% | 4.727 | −0.48% | 4.733 | −0.36% |
| 4.900 | 4.888 | −0.24% | 4.894 | −0.12% | 4.882 | −0.37% | 4.886 | −0.29% |
| 5.000 | 4.980 | −0.40% | 4.987 | −0.26% | 4.967 | −0.66% | 4.984 | −0.32% |

TABLE 2

Results of Test Run 5

| Target Dispense Volume (mL) | Fifth Test Run | % Diff |
|---|---|---|
| 0.100 | 0.098 | −2.00% |
| 0.200 | 0.202 | 1.00% |
| 0.300 | 0.303 | 1.00% |
| 0.400 | 0.402 | 0.50% |
| 0.500 | 0.491 | −1.80% |
| 0.600 | 0.599 | −0.17% |
| 0.750 | 0.752 | 0.27% |
| 0.900 | 0.897 | −0.33% |
| 1.000 | 0.999 | −0.10% |
| 1.100 | 1.101 | 0.09% |
| 1.250 | 1.251 | 0.08% |
| 1.500 | 1.493 | −0.47% |
| 2.000 | 1.992 | −0.40% |
| 3.000 | 2.984 | −0.53% |
| 4.000 | 3.987 | −0.32% |
| 4.250 | 4.242 | −0.19% |
| 4.500 | 4.499 | −0.02% |
| 4.750 | 4.735 | −0.32% |
| 4.900 | 4.898 | −0.04% |
| 5.000 | 4.998 | −0.04% |

As shown in the above tables, the liquid dispensing apparatus maintained a dispense tolerance better than +/−5.0% over the entire dispense range of 0.1 mL to 5.0 mL for each of the test runs. Additionally, the liquid dispensing apparatus maintained a dispense tolerance better than +/−2.0% over the dispense range from 0.5 mL to 5.0 mL for each of the test runs. Additionally, in at least two of the test runs (test runs three and four), the liquid dispensing apparatus maintained a dispense tolerance better than +/−2.0% over the entire dispense range of 0.1 mL to 5.0 mL. Dispense accuracy and precision were not substantially affected by wetting, changes in pipette tips, or changes in pipette bodies.

When introducing elements of the present invention or the embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions and methods without departing from the scope of the invention, it is intended that all matter contained in the above description and shown in the accompanying drawings shall be interpreted as illustrative and not in a limiting sense.

What is claimed is:

1. A system for dispensing radioactive liquids, the system comprising:
    a radiation containment chamber including an enclosure constructed of a radiation shielding material; and
    a liquid dispensing apparatus at least partly disposed in an interior of the enclosure, the liquid dispensing apparatus including:
    a support arm rotatable about a rotation axis;
    an actuator operatively connected to the support arm and configured to at least one of rotate the support arm about the rotation axis and displace the support arm in a direction parallel to the rotation axis;
    a pipette assembly mounted to the support arm, the pipette assembly including a pipette tip defining an opening through which liquids are aspirated and dispensed, a piston, and a stepper motor operatively connected to the piston to control linear displacement of the piston;
    a controller connected to the stepper motor and configured to control the stepper motor to control displacement of the piston, wherein the controller is configured to determine a number of steps by which to rotate the stepper motor based on a non-linear relationship between a volume of liquid aspirated or dispensed by the pipette assembly and a corresponding number of steps by which the stepper motor is rotated.

2. The system of claim 1, wherein the controller is positioned outside of the radiation containment chamber.

3. The system of claim 2, wherein the controller is further configured to:
    receive an input associated with a target transfer volume;
    determine a number of steps by which to rotate the stepper motor based on the input; and
    control a supply of current to the stepper motor based on the determined number of steps to rotate the stepper motor by the determined number of steps.

4. The system of claim 2, wherein the stepper motor is a first stepper motor, and wherein the actuator includes a second stepper motor operatively connected to the support arm to displace the support arm in a direction parallel to the rotation axis, wherein the controller is further configured to:
    control the second stepper motor to position the pipette tip at a first height;
    control the first stepper motor to displace the piston and aspirate a first volume of radioactive liquid from a vial while the pipette tip is positioned at the first height;
    control the second stepper motor to position the pipette tip at a second height lower than the first height; and
    control the first stepper motor to displace the piston and aspirate a second volume of radioactive liquid from the vial while the pipette tip is positioned at the second height.

5. The system of claim 1, wherein the stepper motor is a first stepper motor, and wherein the actuator includes a second stepper motor operatively connected to the support arm and configured to rotate the support arm about the rotation axis, and a third stepper motor operatively connected to the support arm and configured to displace the support arm in a direction parallel to the rotation axis.

6. The system of claim 5 further comprising a support frame including a base and a column extending vertically upward from the base, wherein the second and third stepper motors are positioned within an interior of the column.

7. The system of claim 5, wherein the second and third stepper motors are operatively connected to the support arm through a rotatable shaft, wherein operation of the second stepper motor rotates the shaft, and wherein operation of the third stepper motor displaces the shaft in the direction parallel to the rotation axis, wherein rotation of the rotatable shaft causes the support arm to rotate about the rotation axis, and wherein displacement of the shaft causes the support arm to move in the direction parallel to the rotation axis.

8. The system of claim 1 further comprising a first vial assembly and a second vial assembly, wherein each of the first and second vial assemblies include a vial and a radiation shield at least partially enclosing the vial, and wherein the actuator is configured to rotate the support arm such that the pipette assembly is movable between a first position, in which the pipette assembly is positioned to aspirate a liquid from the vial of the first vial assembly, and a second position, in which the pipette assembly is positioned to dispense the liquid into the vial of the second vial assembly.

9. The system of claim 8, wherein at least one of the vials of the first and second vial assemblies contains a radioactive liquid.

10. The system of claim 9, wherein the radioactive liquid includes one of Germanium-68, Strontium-87m, Technetium-99m, Indium-111m, Iodine-131, and Thallium-201.

11. An apparatus for dispensing radioactive liquids, the apparatus comprising:
    a support arm rotatable about a rotation axis;
    an actuator operatively connected to the support arm, the actuator including a second stepper motor and a third stepper motor, the second stepper motor operatively connected to the support arm and configured to rotate the support arm about the rotation axis, the third stepper motor operatively connected to the support arm and configured to displace the support arm in a direction parallel to the rotation axis; and
    a pipette assembly mounted to the support arm, the pipette assembly including a pipette tip defining an opening through which liquids are aspirated and dispensed, a piston, and a first stepper motor operatively connected to the piston to control linear displacement of the piston;
    wherein the apparatus is free of radiation-sensitive electronics.

12. The apparatus of claim 11, wherein the apparatus is capable of operating for at least 10 cumulative hours within a high radiation area.

13. The apparatus of claim 11, wherein the apparatus is capable of operating for at least 10 cumulative hours in a radioactive field of 5 million millirems per hour.

14. The apparatus of claim 11, wherein the pipette assembly has a dispense capacity of at least 1.0 mL and a dispense tolerance better than +/−5.0% of a target volume over a dispense range of 0.1 mL to 1.0 mL.

15. The apparatus of claim 11, wherein the pipette assembly has a dispense capacity of at least 4.0 mL and a dispense tolerance better than +/−2.0% of a target volume over a dispense range of 0.1 mL to 4.0 mL.

16. The apparatus of claim 11, further comprising a support frame including a base and a column extending vertically upward from the base, wherein the second and third stepper motors are positioned within an interior of the column.

17. A method of dispensing radioactive liquid using a dispensing apparatus including a pipette assembly mounted on a rotatable support arm, the pipette assembly including a pipette tip, a piston, a controller, and a stepper motor operatively connected to the piston, the method comprising:
    positioning the pipette assembly above a first vial using the support arm;
    aspirating a volume of radioactive liquid from a first vial by displacing the piston in a first direction using the stepper motor;
    determining, using the controller, a number of steps by which to rotate the stepper motor based on a non-linear relationship between a volume of liquid aspirated or dispensed by the pipette assembly and a corresponding number of steps by which the stepper motor is rotated;
    rotating the support arm to position the pipette assembly above a second vial; and
    dispensing at least a portion of the volume of radioactive liquid into the second vial by displacing the piston in a second direction opposite the first direction using the stepper motor.

18. The method of claim 17, further comprising receiving, at the controller connected to the stepper motor, an input associated with a target transfer volume, wherein aspirating a volume of radioactive liquid from the first vial includes controlling, using the controller, a supply of current to the stepper motor based on the input to displace the piston in the first direction.

19. The method of claim 18, further comprising:
    controlling, using the controller, the supply of current to the stepper motor based on the determined number of steps.

20. The method of claim 17, wherein aspirating a volume of radioactive liquid from the first vial includes:
    aspirating a first volume of radioactive liquid while the pipette tip is positioned at a first distance from a bottom of the first vial;
    lowering the pipette to a second distance from the bottom of the first vial; and
    aspirating a second volume of radioactive liquid while the pipette tip is positioned at the second distance from the bottom of the first vial.

* * * * *